United States Patent

Davis et al.

[11] Patent Number: 6,068,608
[45] Date of Patent: May 30, 2000

[54] METHOD OF USING INTEGRAL AORTIC ARCH INFUSION CLAMP

[75] Inventors: Albert Davis, Richardson; Wendel Lloyd, Dallas; Christina Draper, Dallas; Mitta Suresh, Dallas; David Hernon; Richard C. Bryant, both of Richardson, all of Tex.

[73] Assignee: Chase Medical, Inc., Richardson, Tex.

[21] Appl. No.: 08/846,654

[22] Filed: May 1, 1997

[51] Int. Cl.[7] .................................................. A61M 37/00
[52] U.S. Cl. ................................................. 604/4; 604/96
[58] Field of Search .................................... 604/174–175, 604/96, 1–2, 4–6; 128/207.15; 606/159, 192; 600/16–18, 569, 572

[56] References Cited

U.S. PATENT DOCUMENTS

| | | |
|---|---|---|
| Re. 35,352 | 10/1996 | Peters . |
| Re. 35,459 | 2/1997 | Jonkman . |
| 2,701,559 | 2/1955 | Cooper . |
| 3,640,282 | 2/1972 | Kamen et al. . |
| 4,129,129 | 12/1978 | Amrine . |
| 4,328,056 | 5/1982 | Snooks . |
| 4,413,989 | 11/1983 | Schjeldahl et al. . |
| 4,417,576 | 11/1983 | Baran . |
| 4,423,725 | 1/1984 | Baran et al. . |
| 4,531,936 | 7/1985 | Gordon . |
| 4,592,340 | 6/1986 | Boyles . |
| 4,596,552 | 6/1986 | DeVries . |
| 4,601,706 | 7/1986 | Aillon . |
| 4,610,662 | 9/1986 | Weikl et al. ................................ 604/53 |
| 4,648,384 | 3/1987 | Schmukler . |
| 4,676,778 | 6/1987 | Nelson, Jr. ................................ 604/45 |
| 4,689,041 | 8/1987 | Corday et al. . |
| 4,741,328 | 5/1988 | Gabbay . |
| 4,781,682 | 11/1988 | Patel . |
| 4,927,412 | 5/1990 | Menasche . |
| 4,943,277 | 7/1990 | Bolling . |
| 4,988,515 | 1/1991 | Buckberg . |
| 5,011,469 | 4/1991 | Buckberg et al. . |
| 5,013,296 | 5/1991 | Buckberg et al. . |

(List continued on next page.)

FOREIGN PATENT DOCUMENTS

| | | |
|---|---|---|
| 0 266 957 A2 | 10/1987 | European Pat. Off. . |
| 0 280 25 | 2/1988 | European Pat. Off. . |
| 0 417 781 A1 | 9/1990 | European Pat. Off. . |
| 0 664 104 A2 | 1/1995 | European Pat. Off. . |
| 0 218 275 | 8/1996 | European Pat. Off. . |
| 1547-328 | 6/1979 | United Kingdom . |
| WO 95/17919 | 6/1995 | WIPO ........................... A61M 25/01 |
| WO 95/32756 | 12/1995 | WIPO . |
| WO 96/30072 | 3/1996 | WIPO ........................... A61M 29/00 |
| WO 96/40347 | 12/1996 | WIPO . |

*Primary Examiner*—Mark Bockelman
*Attorney, Agent, or Firm*—Robert C. Klinger

[57] ABSTRACT

An improved method of using a single catheter to infuse blood to the heart, clamping the aorta and delivering a cardioplegia solution. Patient trauma is significantly reduced using a single cannulation. A single catheter (10, 90, 92) is used having a unique balloon (56, 93, 102) for occluding the aorta. In a first embodiment, a single catheter (10) is positioned upwardly in the aorta to infuse oxygenated blood into the ascending aorta via an infusion lumen (72) terminating at the distal end (54), with cardioplegia solution being delivered via openings (82) defined closely adjacent the balloon (56) on the proximal side of the balloon. The inflated balloon (56) isolates the two delivery openings (72,82) from one another to facilitate use of an extracorporeal circuit. In a second embodiment, a single catheter (90) can be positioned downwardly in the aorta to infuse blood via openings (82) into the ascending aorta proximate the subclavian artery, and deliver cardioplegia solution via the distal opening (72) downward toward the aortic base. The balloon (102) is preferably filled with a partitioned resilient material (104) to permit varying diameters of the balloon and occlude body passageways having varying diameters and curvatures.

24 Claims, 7 Drawing Sheets

U.S. PATENT DOCUMENTS

| | | | |
|---|---|---|---|
| 5,021,045 | 6/1991 | Buckberg et al. . | |
| 5,024,668 | 6/1991 | Peters et al. . | |
| 5,033,998 | 7/1991 | Corday et al. | 600/18 |
| 5,090,960 | 2/1992 | Michael | 604/101 |
| 5,135,474 | 8/1992 | Swan et al. | 604/8 |
| 5,135,484 | 8/1992 | Wright | 604/28 |
| 5,149,330 | 9/1992 | Brightbill . | |
| 5,151,087 | 9/1992 | Jonkman . | |
| 5,167,628 | 12/1992 | Boyles . | |
| 5,171,218 | 12/1992 | Fonger et al. . | |
| 5,192,290 | 3/1993 | Hilal . | |
| 5,197,952 | 3/1993 | Marcadis et al. . | |
| 5,213,576 | 5/1993 | Abiuso et al. . | |
| 5,221,258 | 6/1993 | Shturman . | |
| 5,232,444 | 8/1993 | Just et al. . | |
| 5,290,231 | 3/1994 | Marcadis et al. . | |
| 5,308,323 | 5/1994 | Sogawa et al. . | |
| 5,308,325 | 5/1994 | Quinn et al. . | |
| 5,312,344 | 5/1994 | Grinfeld et al. | 604/101 |
| 5,324,260 | 6/1994 | O'Neill et al. | 604/96 |
| 5,334,142 | 8/1994 | Paradis | 604/53 |
| 5,338,298 | 8/1994 | McIntyre | 604/96 |
| 5,360,403 | 11/1994 | Mische | 604/101 |
| 5,378,230 | 1/1995 | Mahurkar | 604/43 |
| 5,395,330 | 3/1995 | Marcadis et al. | 604/96 |
| 5,395,331 | 3/1995 | O'Neill et al. | 604/96 |
| 5,423,745 | 6/1995 | Todd et al. | 604/53 |
| 5,433,700 | 7/1995 | Peters | 604/4 |
| 5,437,637 | 8/1995 | Lieber et al. | 604/96 |
| 5,439,444 | 8/1995 | Andersen et al. . | |
| 5,443,446 | 8/1995 | Shturman | 604/49 |
| 5,443,448 | 8/1995 | DeVries | 604/96 |
| 5,451,204 | 9/1995 | Yoon . | |
| 5,451,207 | 9/1995 | Yock | 604/53 |
| 5,452,733 | 9/1995 | Sterman et al. | 128/898 |
| 5,458,574 | 10/1995 | Machold et al. | 604/101 |
| 5,458,575 | 10/1995 | Wang | 604/101 |
| 5,478,309 | 12/1995 | Sweezer et al. | 604/4 |
| 5,487,730 | 1/1996 | Marcadis et al. . | |
| 5,501,667 | 3/1996 | Verduin, Jr. . | |
| 5,505,598 | 4/1996 | Boothe t al. . | |
| 5,533,957 | 7/1996 | Aldea . | |
| 5,558,644 | 9/1996 | Boyd et al. . | |
| 5,571,215 | 11/1996 | Sterman et al. . | |
| 5,584,803 | 12/1996 | Stevens et al. . | |
| 5,597,377 | 1/1997 | Aldea . | |
| 5,609,571 | 3/1997 | Buckberg et al. . | |
| 5,611,775 | 3/1997 | Machold et al. . | |
| 5,616,149 | 4/1997 | Barath . | |
| 5,620,418 | 4/1997 | O'Neill et al. . | |
| 5,658,311 | 8/1997 | Baden . | |
| 5,662,620 | 9/1997 | Lieber et al. . | |

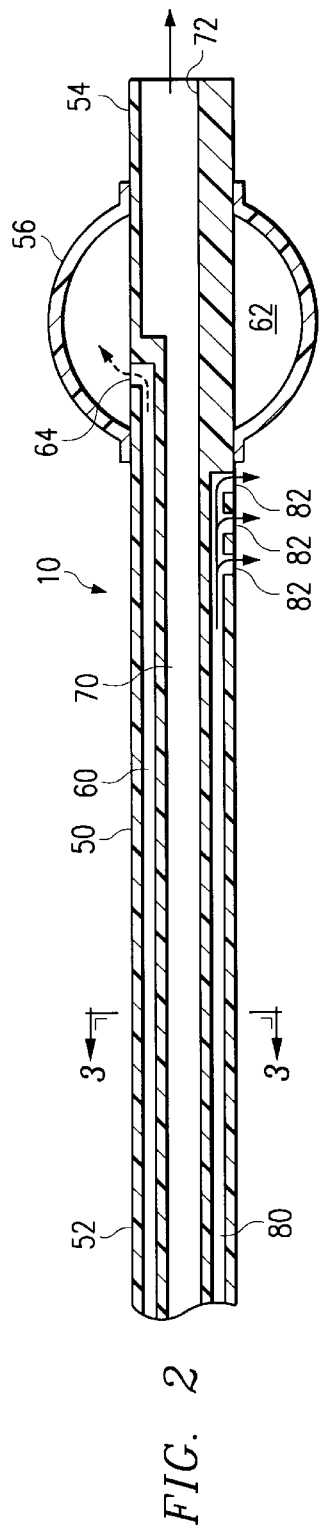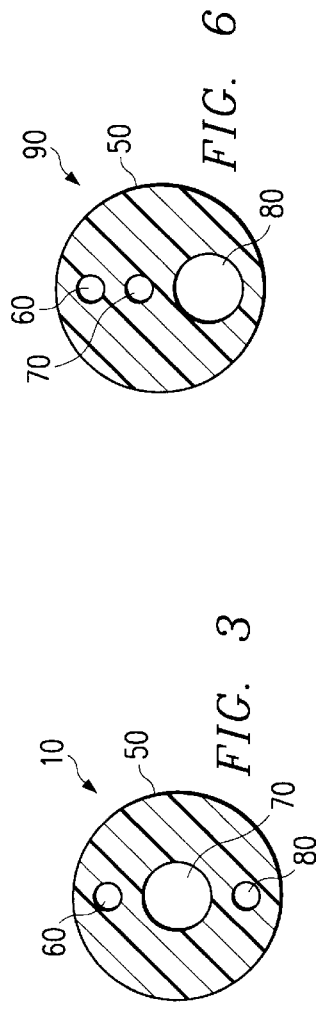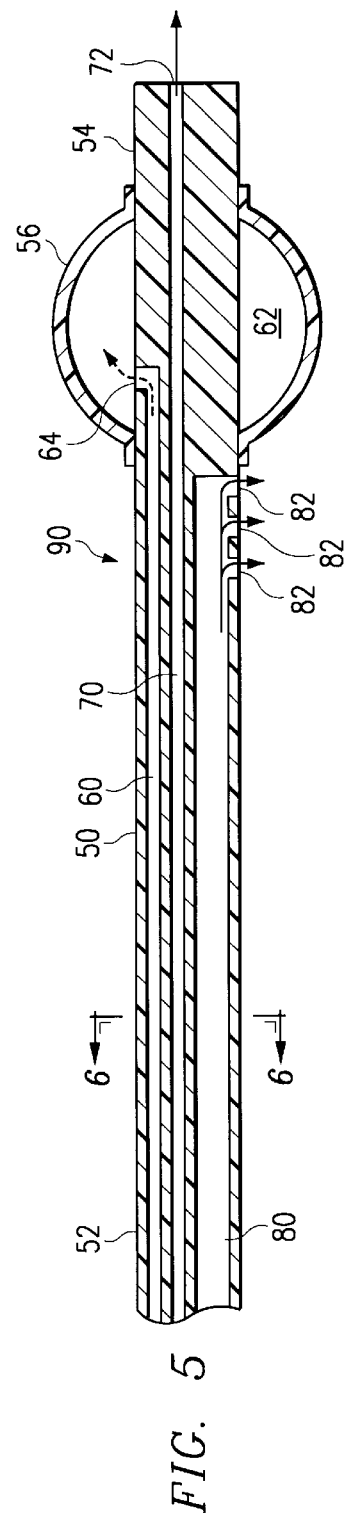

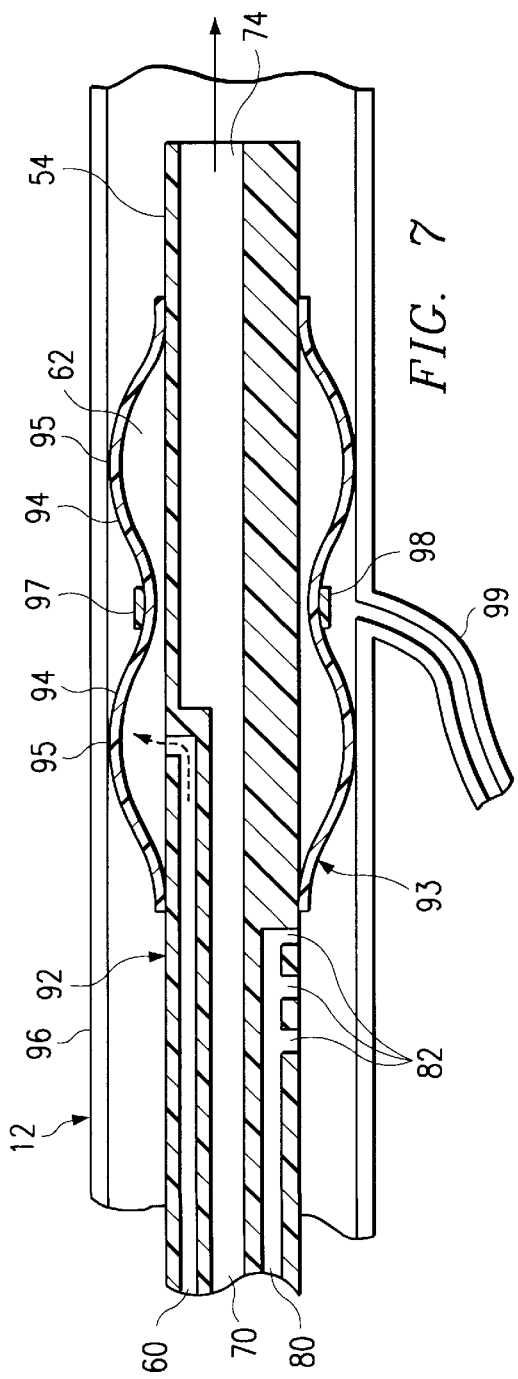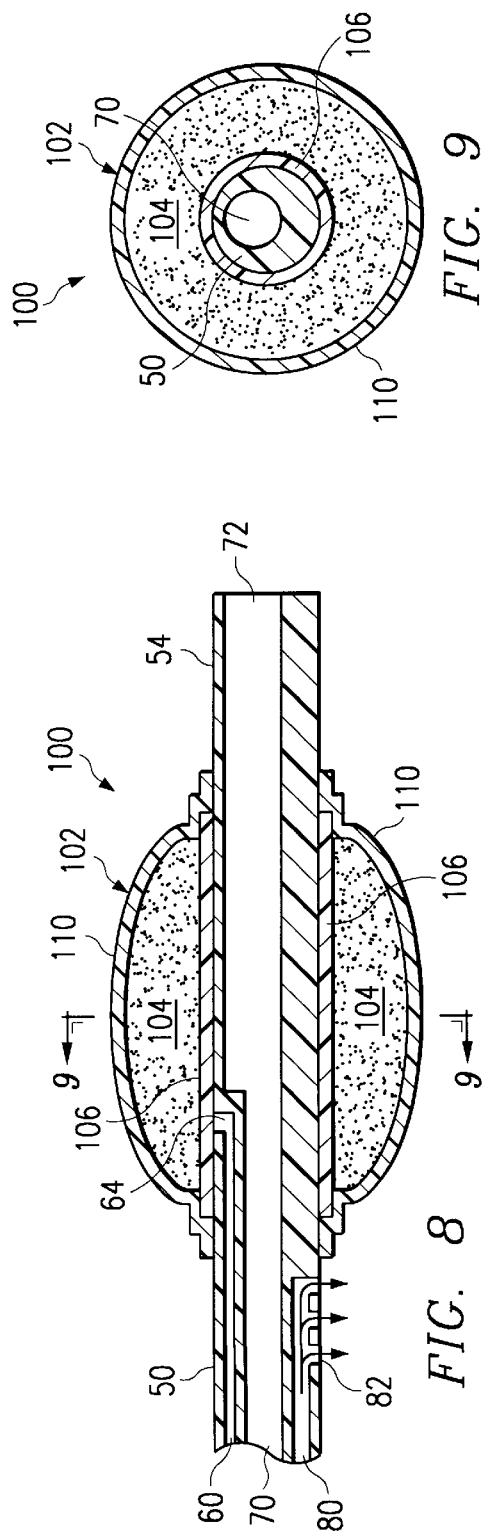

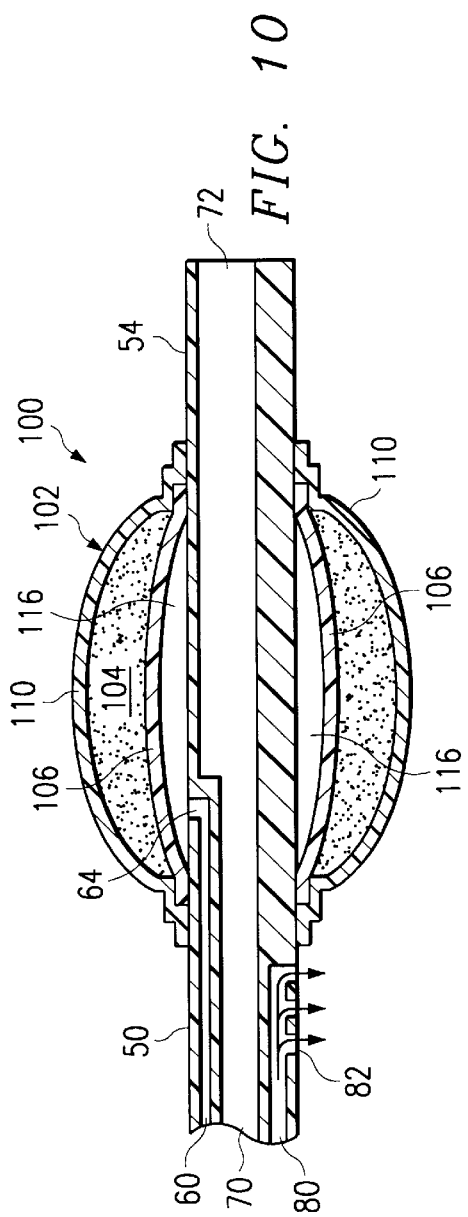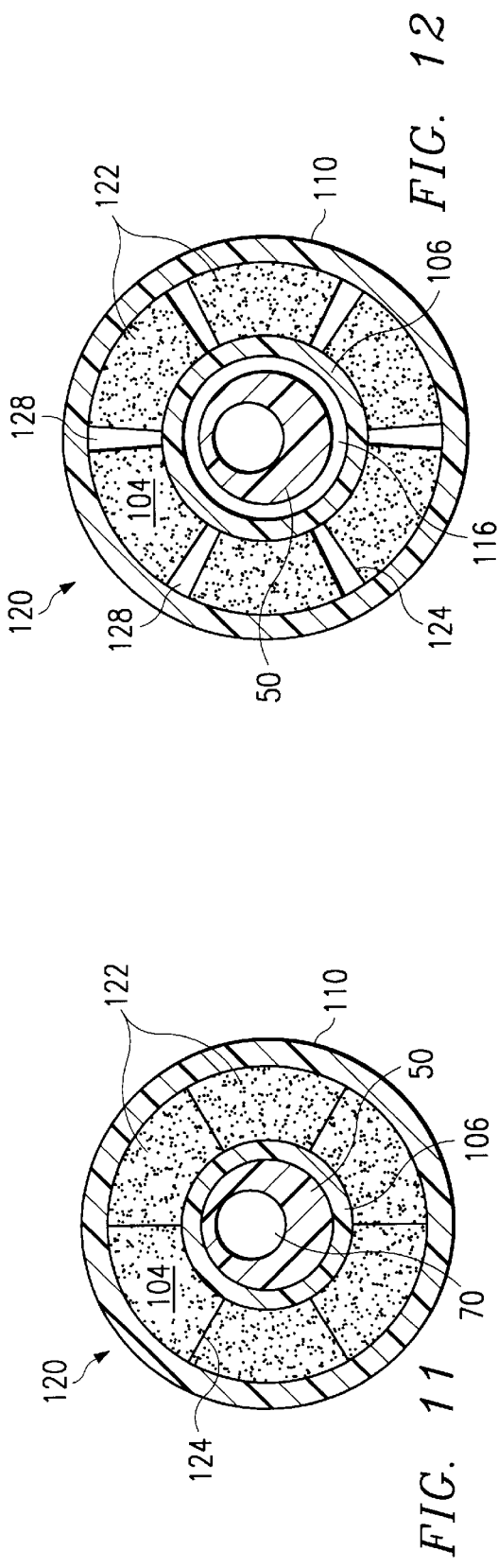

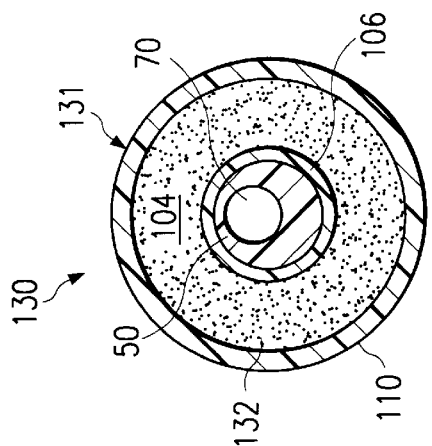
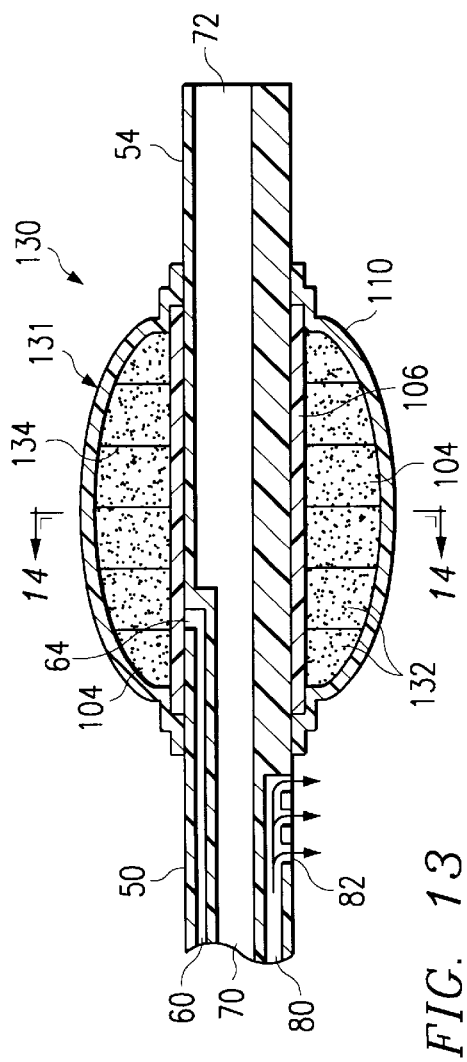
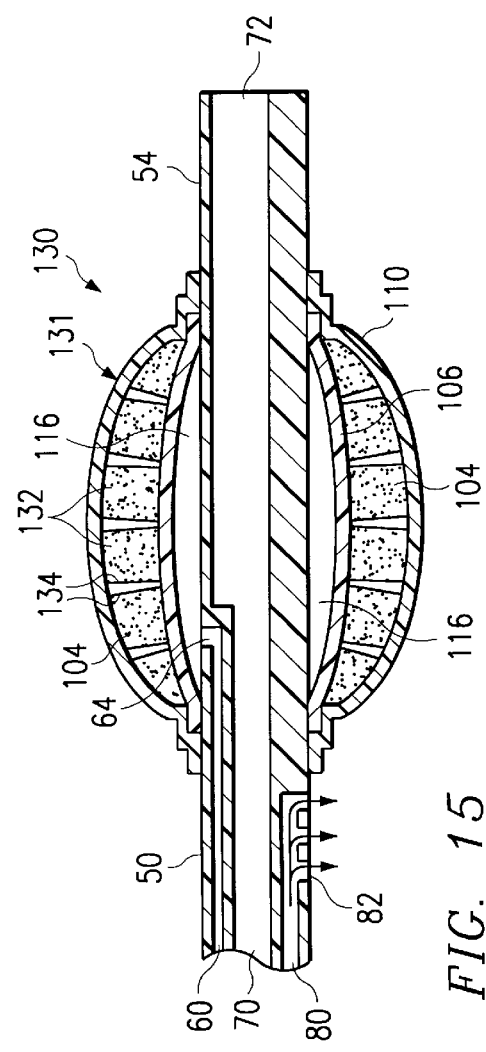

METHOD OF USING INTEGRAL AORTIC ARCH INFUSION CLAMP

CROSS REFERENCE TO RELATED APPLICATIONS

Cross reference is made to the commonly assigned patent application Attorney's Docket Chase 03 entitled INTEGRAL AORTIC ARCH INFUSION CLAMP CATHETER filed herewith.

FIELD OF THE INVENTION

The present invention is generally related to cardiac catheters including venous perfusion and arterial perfusion cardiac catheters for providing cardiopulmonary bypass support and isolation of the heart while performing open heart surgery, and more particularly to an improved method for providing infusion of oxygenated blood, aortic clamping, and delivery of a cardioplegia solution.

BACKGROUND OF THE INVENTION

Use of catheters to administer fluids to and draw out of the body has been a standard practice in medical procedures for years. Multiple catheters are typically used to connect an extracorporeal circuit to the body during open heart procedures. The various catheters are simultaneously used to provide different functions, one catheter for delivering a cardioplegia solution, with another catheter being inserted into the heart to infuse oxygenated blood to the ascending aorta.

In a typical open heart procedure, blood is bypassed from the heart and lungs to a heart lung machine. When bypassing the heart, the blood is siphoned away from the superior vena cava and inferior vena cava, oxygenated, and then returned to the ascending aorta. The primary reason for using the extracorporeal circuit is to provide an empty and bloodless heart for the surgeon to effectively perform repair. In spite of bypassing the blood from the heart, the heart muscle will still beat, primarily for two reasons. First, the heart muscle is still receiving oxygenated blood from the extracorporeal circuit. Secondly, the heart's electrochemical activity is still functioning normally.

In a typical open heart procedure, the aorta is cannulated in two locations. In a first location, the aorta is cannulated with a first catheter for returning oxygenated blood to the body from the extracorporeal circuit. Oxygenated blood is delivered to the heart with a catheter through the coronary arteries from the base of the aorta, known as the aortic base. To stop the flow of oxygenated blood to the heart, the ascending aorta is typically clamped distal to the coronary ostia, known as the opening for coronary arteries with a large stainless steel aortic cross clamp. Clamping the ascending aorta isolates the coronary arteries from the extracorporeal circuit.

The aorta is cannulated in a second location using a second catheter to deliver cardioplegia. The electrochemical action of the heart can be stopped by infusing the heart muscle with a cardioplegia solution. Cardioplegia solution is typically rich in potassium ions. The potassium ions interrupt the heart's electrical signals, resulting in a still heart. Stopping the heart gives a stable platform to effectively conduct the necessary repairs to the heart. The cardioplegia solution is delivered to the heart muscle through the coronary arteries. This is typically accomplished by infusing the cardioplegia solution into the ascending aorta with the second catheter between the large cross clamp and the aortic valve located at the base of the aorta. The cross clamp keeps the cardioplegia and the oxygenated blood separated from one another.

There are three areas of concern in performing surgery in this conventional, multi-cannulation approach. First, clamping the aorta exerts tremendous force on the aortic walls, and there is a potential for the arteriosclerotic plaque deposits on the aortic walls to dislodge. Due to the proximity of the cross clamp to the carotid artery, this poses a special threat since the dislodged plaque can potentially go straight to the brain, resulting in a stroke to the patient. Secondly, the clamping pressure also causes damage to the delicate endothelial lining of the aorta, which is the inner surface of the artery. Post operative scaring of the endothelial lining can provide an irregular surface causing increased arteriosclerotic plaque build up. Finally, the two cannula suture sites created by the cardioplegia cannula and arterial return cannula tend to scar the aorta and make it very difficult to find suitable cannulation sites for open heart procedures in the future, if necessary.

One prior art method of addressing the short comings of current multi-cannulation procedures is by percutaneously accessing venous and arterial blood femorally, such as disclosed in U.S. Pat. No. 5,478,309 to Sweeter, et al. This method, however, is cumbersome and is dependent on the skill level of the surgeon. Moreover, this percutaneous approach is a major deviation from the conventional methods.

Alternatively, cardioplegia can be delivered through the coronary sinus in conventional ways. Although this alternative approach helps avoid one incision in the aorta, another incision is required in the right atrium, and the aortic clamp is still needed.

There is a desire to provide an improved method for infusing the heart with oxygenated blood and delivering cardioplegia solution in a more atraumatic way.

There is also a desire to provide an improved method for occluding a body vessel, such as the aorta, that has a varying diameter and curvature.

SUMMARY OF THE INVENTION

The method of the present invention achieves technical advantages by using only one unique catheter to accomplish all three functions of 1) infusing blood, 2) delivering cardioplegia solution, and 3) occluding the aorta. The method uses a unique catheter inserted into the ascending aorta that has a uniquely designed balloon at the distal end thereof which inflates to occlude the aorta and act as a clamp. An infusion opening is provided at the distal end of the catheter and infuses oxygenated blood into the ascending aorta above the balloon. The cardioplegia solution is delivered through a separate opening adjacent and proximal to the balloon to deliver cardioplegia to the coronary arteries at the aortic base. The catheter is a multi-lumen tube wherein the largest lumen is used for delivering the oxygenated blood to the ascending aorta. A first lumen is used for infusing the oxygenated blood, a second lumen is used to inflate or deflate the balloon, and the third lumen is used to infuse the cardioplegia solution.

According to the first preferred method of the present invention, the need for a cross clamp is eliminated as the novel expandable balloon is used to occlude the aorta. The balloon preferably is filled with a resilient material, such as foam or a gel to provide a gentle atraumatic force that expands inside the aorta, and significantly reduces potential damage to the endothelial layer of the aorta. Additionally, the elimination of the cross clamp reduces the potential for any arteriosclerotic plaque to dislodge from the aorta. Only one moderate size incision is required into the ascending aorta for insertion of the catheter, which reduces the necessary trauma to the heart.

According to the preferred method of the present invention, the integral infusion catheter is inserted into the ascending aorta such that the catheter distal end extends upwardly into the ascending aorta to infuse oxygenated blood out the distal end of the catheter proximate the expanded balloon. The cardioplegia solution is delivered via an opening closely proximate and at the other side of the balloon, the opening being defined on the proximal side of the balloon. The cardioplegia opening may also be used to intermittently administer oxygenated blood to the heart muscle and coronary artery. Preferably, the balloon is positioned in the ascending aorta such that the balloon resides above the aortic base with oxygenated blood being infused into the aortic arch. More specifically, the balloon is positioned between the aortic base and the subclavian artery.

In an alternative method of the present invention, the catheter can be inserted into the ascending aorta in the reverse orientation. That is, the distal end of the catheter can be directed downwardly toward the aortic base, with the cardioplegia solution being dispensed out the distal end of the catheter. The opening on the other side of the balloon, which is defined between the balloon and the catheter proximal end, is used to infuse oxygenated blood into the ascending aorta.

In yet a further alternative embodiment, the balloon is uniquely designed to be filled with, or encompassed by, a resilient material such as a foam or gel to provide a nominal diameter when no pressure is applied. The resilient material is preferably partitioned into sections to facilitate further expansion of the balloon in a body vessel having a varying diameter or curvature.

In still yet a further embodiment of the invention the balloon may have 2 lobes defining a cavity therebetween when inflated in the aorta to create a bloodless region. This bloodless region facilitates performing an anastomosis in a clear field when attaching a saphenous vein to the aorta.

Irregardless of which method is utilized, a single multi-lumen catheter is utilized which requires only one incision in the ascending aorta. The catheter provides the three necessary functions of occluding the aorta, infusing oxygenated blood, and delivering the cardioplegia solution. The method of using the catheter having the uniquely designed balloon is adapted for occluding any body vessel having a varying diameter and curvature, such as the trachea.

DESCRIPTION OF THE DRAWINGS

FIG. 2 is a sectional side view of the integral catheter utilized to conduct the method in FIG. 1, the catheter shown as having three lumens, the first for inflating the balloon, the second for infusing oxygenated blood out the distal end of the catheter proximate the balloon, and the third lumen for dispensing a cardioplegia solution closely proximate the balloon and proximal of the balloon;

FIG. 3 is a cross section of the catheter taken along lines 3—3 in FIG. 2 illustrating the location and relative diameters of the three lumens;

FIG. 5 is a sectional side view of an integral catheter utilized to conduct the method in FIG. 4, wherein the larger lumen terminates proximal of the balloon to infuse blood proximal of the downwardly extending catheter;

FIG. 6 is a cross section of the catheter taken along lines 6—6 in FIG. 5 illustrating the location and relative diameters of the three lumens;

FIG. 7 is a cross section of a catheter according to an alternative preferred embodiment having a double lobe balloon for creating a bloodless region in the aorta to perform an anastomosis of an artery;

FIG. 8 is a sectional sideview of a catheter according to an alternative preferred embodiment of the present invention suitable for occluding any body passageway, such as the aorta, seen to comprise an inner shell with a resilient material disposed thereabout and preferably encapsulated by an outer shell, the balloon having a nominal diameter when no pressure is applied, and an increased diameter when a pressure is applied to further expand the balloon;

FIG. 9 is a cross section of the balloon in FIG. 8 taken along line 9—9 to illustrate the resilient foam material encapsulated between the inner balloon shell and the outer balloon shell;

FIG. 10 is an illustration of the catheter of FIG. 8 in the expanded state with a pressure applied to the inner balloon shell, compressing the resilient foam material to further expand the overall diameter of the balloon;

FIG. 11 is a sectional view of an alternative preferred embodiment of the catheter shown in FIG. 8 whereby the resilient foam material is partitioned into sections, each section being separated by radially extending opposing edges about the catheter body;

FIG. 12 is a sectional view also taken along line 9—9 in FIG. 8 illustrating the embodiment of FIG. 11 in the expanded state, with the resilient foam sections expanding radially outward and away from one another to further increase the diameter of the catheter when pressure is applied to the balloon via the associated lumen;

FIG. 13 is yet another alternative preferred embodiment of the present invention from that of FIG. 8 and FIG. 11, when the resilient foam material is partitioned in the transverse direction with respect to the catheter body;

FIG. 14 is a sectional side view taken along line 14—14 in FIG. 13 illustrating the annular resilient foam sections;

FIG. 15 is a sectional side view of the catheter of FIG. 13 illustrating the balloon in the expanded state, whereby the annular resilient foam sections expand outwardly and away from one another as pressure is applied via the associated balloon lumen to expand the outer balloon shell and increase the overall diameter of the balloon as a function of the pressure applied.

DETAILED DESCRIPTION OF THE PREFERRED EMBODIMENT OF THE PRESENT INVENTION

Figure 1:
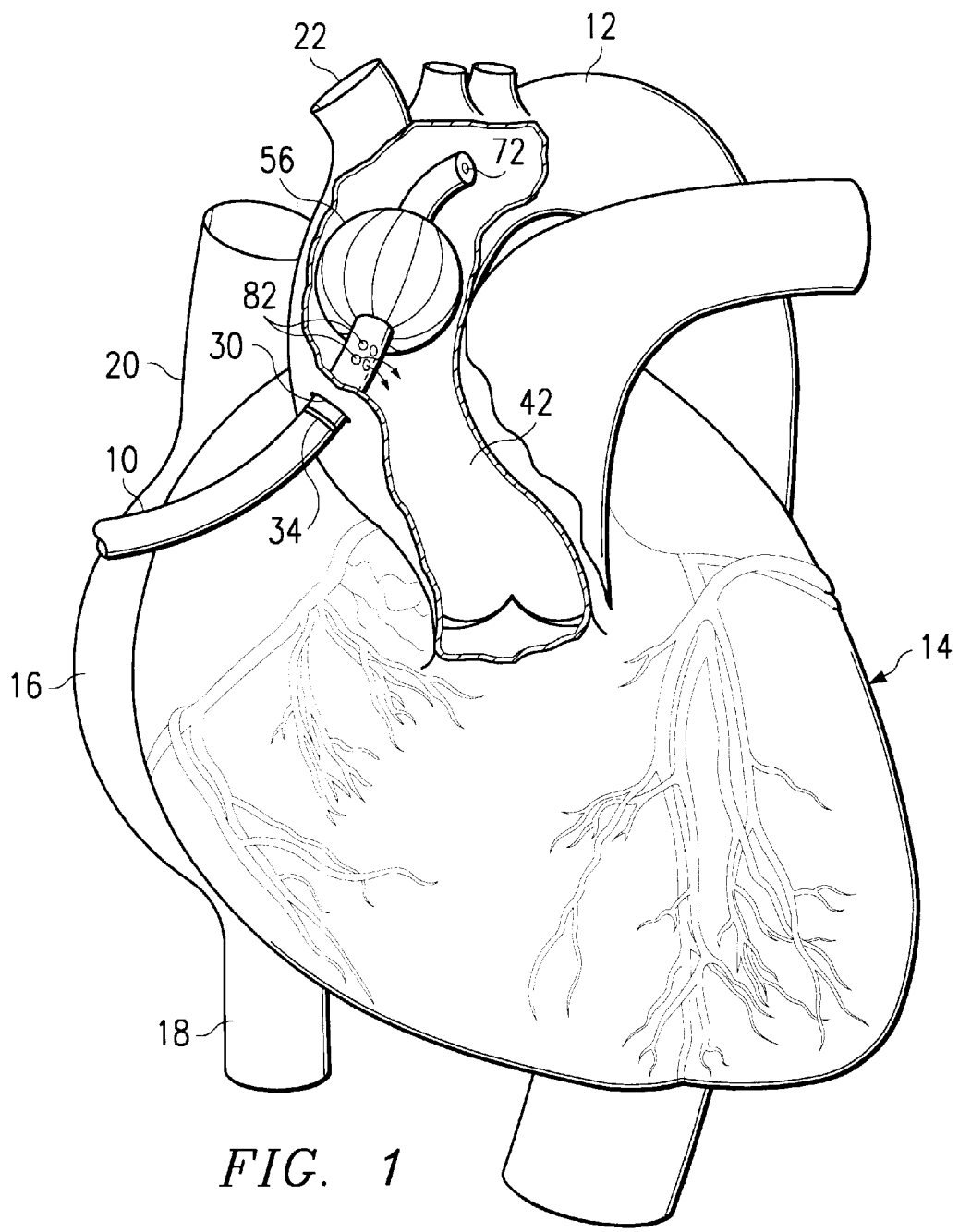
FIG. 1 is an illustration of a single multi-lumen catheter properly inserted into the ascending aorta according to the preferred method of the present invention.

First with reference to FIG. 1, there is shown the first preferred method of the present invention. As shown in FIG.

1, a single multi-lumen catheter 10 is utilized for cannulating the ascending aorta 12 of a human heart 14. For reference purposes, the right atrium is shown at 16, with the inferior vena cava being shown at 18 and superior vena cava being shown at 20. The subclavian artery is shown at 22.

Catheter 10 is upwardly positioned within the ascending aorta 12, as shown, by first creating a suitable incision in the aorta proximate the aortic base, shown at 30. The distal end 32 of catheter 10 is inserted into the incision of the aorta just over the aortic base, with the distal end 32 being advanced upwardly into the ascending aorta 12 until a reference marker 34 of catheter 10 is located adjacent incision 30. As shown in FIG. 1, the distal end 72 is oriented upwardly proximate the subclavian artery 22. An inflatable balloon 56 of catheter 10 is carefully positioned between the aortic base but ahead of the left subclavian artery 22. In this orientation, a plurality of cardioplegia delivery openings 82 are oriented above and proximate the aortic base 42 of the heart.

When the surgeon is prepared to put the patient on the extracorporeal circuit, the balloon 56 is inflated with air or a saline solution until the balloon's force can be felt by the surgeon's hand outside the aortic walls. This pressure assures that the aorta is fully occluded. Just prior to inflating the balloon, the main lumen of the catheter is connected to an oxygenated blood source and infuses oxygenated blood out of the distal end of the catheter into the ascending aorta 12. When the balloon is fully inflated, the patient is properly connected to the extracorporeal circuit.

Next, a predetermined quantity of cardioplegia solution is delivered via the cardioplegia openings 82. This cardioplegia solution is provided to the aorta between the aortic valve and the balloon clamp. The electrochemical action of the heart is stopped by infusing the heart muscle with the cardioplegia solution. This cardioplegia solution is typically rich in potassium ions, which potassium ions interrupt the heart electrical signals resulting in a still heart. Stopping the heart gives a stable platform to effectively conduct the necessary procedures to the heart.

It is particularly noted according to the present invention that only one moderate incision 30 is required to cannulate the ascending aorta 12 to achieve all three functions. This significantly reduces the trauma to the aorta as compared to other conventional and alternative approaches. Since the inflatable balloon is utilized to occlude the ascending aorta, the need for a cross clamp is eliminated, and the possibility of dislodging plaque is significantly reduced. In addition, the delicate endothelial lining of the aorta is gently engaged.

Referring now to FIG. 2, there is shown a side sectional view of an integral catheter 10 which is suited for achieving the method of the present invention. Catheter 10 is seen to include an elongated catheter body 50 extending between a proximal end 52 and a distal end 54. Provided at the distal end of catheter 10 is an inflatable balloon 56 which is secured circumferentially about the catheter by an adhesive or other suitable affixing means. The balloon 56 may be filled with a foam or other resilient material, or simply left empty. A first smaller lumen 60 extends longitudinally through catheter 10 and is in fluid communication within the interior 62 of balloon 56 via an opening 64 defined through body 50. A larger, second lumen 70 extends longitudinally from the catheter proximal end through catheter 10 and opens at a distal opening 72 at distal end 54. A smaller third lumen 80 extends from the proximal end of catheter 10 and terminates via a plurality of openings 82 defined through body 50. The openings 82 are necessarily provided closely adjacent to the expandable balloon 56, but on the proximal side of the balloon, opposite the infusion distal opening 72. Thus, openings 72 and 82 are provided on opposite sides of balloon 56. In use, the inflated balloon 56 sealingly isolates openings 72 and 82 from one another for infusing blood out one side, and delivering cardioplegia solution out the other.

Catheter body 50 is preferably comprised of suitable flexible plastic material, such as silicone, PVC or other thermoplastics according to well known techniques. Preferably, the diameter of the main infusion lumen 70 is 0.250 inches. The diameter of the smaller inflating lumen 60 is about 0.030 inches, and the cardioplegia lumen 82 has a diameter of about 0.100 inches.

Referring to FIG. 3, the relative diameters and locations of the three lumens are shown, again, with the main infusion lumen 70 having the largest diameter for delivering oxygenated blood to the ascending aorta.

Sometimes the surgeon may find it necessary to perfuse oxygenated blood to the heart muscle and the coronary artery instead of delivering cardioplegia. This can be accomplished using catheter 10 according to the present invention by selectively administering oxygenated blood to the heart muscle and coronary artery through the cardioplegia lumen 80 via openings 82. Cardioplegia and oxygenated blood can be alternately administered above the aortic base to control the response of the heart muscle to the cardioplegia during surgery, and assisting the heart in resuming a normal beat after surgery.

Figure 4:
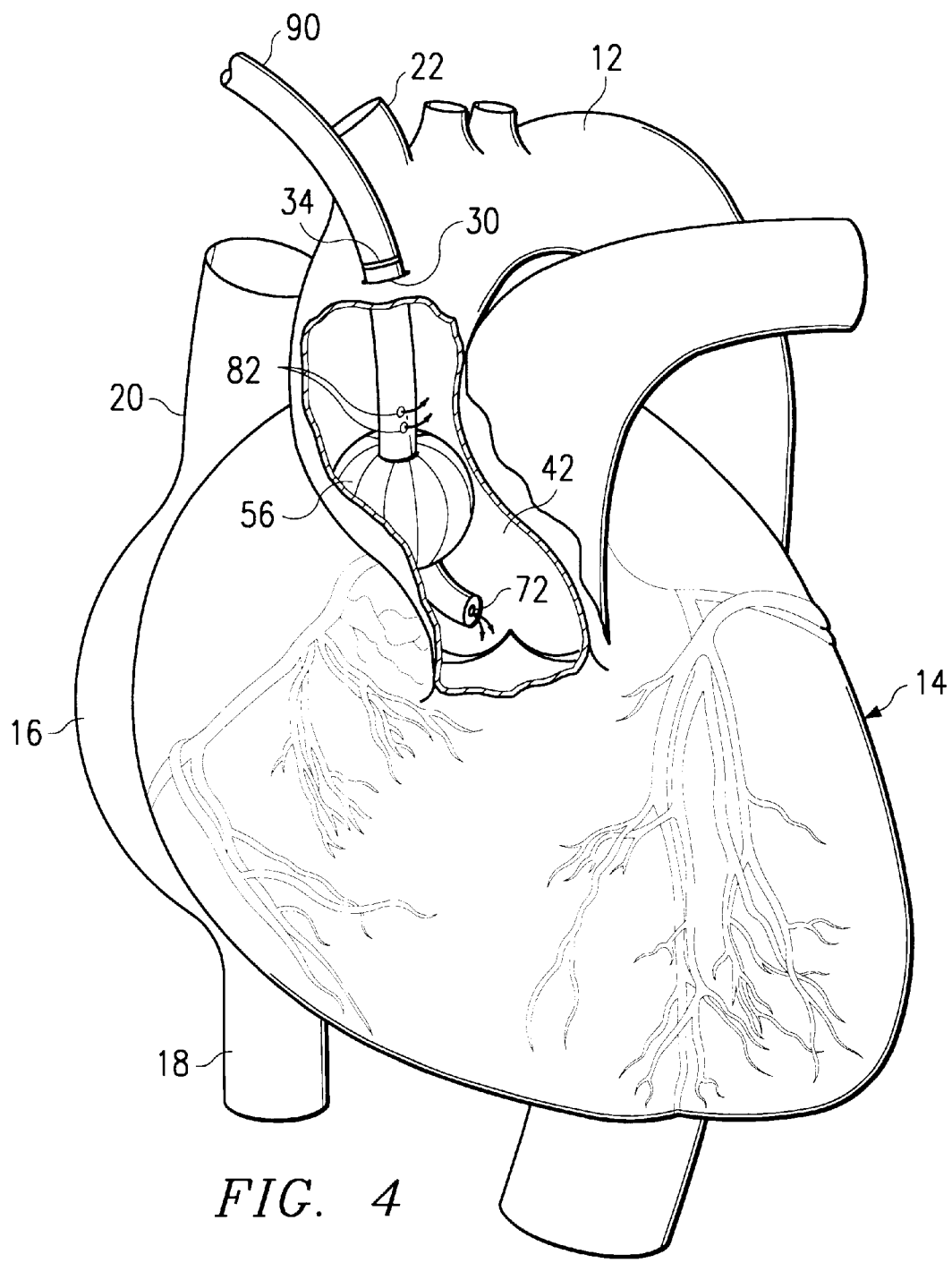
FIG. 4 is an illustration of an alternative preferred method of the present invention whereby the single multi-lumen catheter is inserted into the ascending aorta with the catheter distal end oriented toward the aortic base for delivery of the cardioplegia solution to the aortic base, with the oxygenated blood being infused via catheter openings closely proximate the balloon and proximal of the balloon, as shown.

Turning now to FIG. 4, there is shown an alternative method of the preferred invention whereby the orientation of a catheter 90 in the aorta is reversed. That is, the catheter 90 is inserted into incision 32 of the ascending aorta 12, but at a location further upward than that shown in FIG. 1, close to the subclavian artery 22 such that the catheter 90 extends downwardly, as shown. The distal end 54 of the catheter is advanced proximate the aortic base 42 and delivers cardioplegia solution therefrom. The openings 82 proximate balloon 56 are positioned above the balloon 56, toward to subclavian artery 22 for infusion of oxygenated blood into the ascending aorta 12.

Referring to FIG. 5, wherein like numerals refer to like elements, in this embodiment the diameter of the lumen 80 infusing blood into the ascending aorta is designed to have a much larger diameter than either the lumen 70 delivering cardioplegia solution to the distal end of the catheter or lumen 60 for inflating balloon 56. The diameter of the third lumen 80 of catheter 90 is increased to have a diameter of between 0.250 and 0.350 inches for providing a suitable flow rate of oxygenated blood via openings 82 to the ascending aorta. The diameter of the second lumen 70 delivering the cardioplegia solution out distal opening 72 is reduced to about 0.060 inches, which is suitable to deliver the necessary quantity of cardioplegia to the heart. The diameter of the first lumen 60 is still 0.040 inches for inflating balloon 56. FIG. 6 shows the relative orientation and diameters of the lumens of FIG. 5, taken along line 6—6.

In both preferred methods of the present invention shown in FIGS. 1 and 4, only one moderate incision of approximately 0.5 inches in length is required to be provided in the ascending aorta 12 for insertion of catheter 10 and catheter 90. This reduces the overall trauma to the aorta as compared to other alternative and conventional approaches. Moreover, use of balloon 56 to occlude the aorta reduces trauma to the aorta, and significantly reduces the chance that plaque will be dislodged which could result in a stroke to the patient. The endothelial lining of the aorta is maintained. The methods of the present invention can be performed relatively quick by the surgeon, which reduces cost and the possibility of further complications as compared to multiple cannulation of the aorta.

The catheter body 50 is sufficiently flexible to allow maneuverability without kinking in the ascending aorta, allowing easy manipulation of the catheter within the aorta as shown in FIG. 1 and FIG. 4. If desired, the catheter could be designed to be extra resilient between the proximal end and opening 82 to further allow maneuverability of the catheter without kinking at the cannulation site 34.

The longitudinal compactness of the operative features of both catheters 10 and 90 facilitate the effective use of the single catheter. The inflated balloon 56 typically has a diameter of about 1 inch, with the several openings 82 being provided immediately adjacent the balloon 56, and with the distal end and opening 72 being no more than 0.5 inches from balloon 56, as shown. The overall distance between the proximal openings 82 and the distal end 54 of catheter 50 is ideally no more than about 2 inches for a use in the typical human heart. Thus, the dimensions to these features of the catheters 10 and 90 is critical to facilitate effective use of the present invention.

Typically during a bypass surgery the blocked artery is bypassed by attaching a saphenous vein graft to the artery distal to the occlusion while the other end of the graft is attached to the aorta. The surgeon typically performs an anastomosis to the artery first, followed by the anastamosis to the aorta. Since the aorta is filled with blood or cardioplegia, the surgeon may not have good visibility when an incision is made in the aorta. This reduces his ability to perform the anastamosis. To avoid this problem and to enhance the visibility during the surgery, a catheter having a specially shaped balloon can be used. A catheter 92 having a balloon 93 shown in FIG. 7 is suitable, and has two bulbs or lobes 94 creating two seals 95 with the adjacent wall 96 of the aorta 12. The area 97 in between these two bulbs 94 creates a bloodless area for the surgeon to perform the anastomosis in a clear field.

Referring to FIG. 7, wherein like numerals refer to like elements, there is shown catheter 92 whereby the single balloon 93 is formed to have two lobes or bulbs 94 by securing an annular constriction, such as a ring 98 about the midsection of the balloon 93, allowing the two lobes 94 to remain in fluid communication with each other for inflation by the single inflation lumen 60. The ring 98 is preferably secured to balloon 93 with a suitable adhesive. Alternatively, the balloon 93 could simply be formed to have two lobes without the need for a ring, but this approach is more intricate and expensive. Similarly, two separate balloons comprising a proximal balloon and a distal balloon could be provided, both in fluid communication with lumen 60 if desired, the proximal balloon being no more than 3 inches from the catheter distal end. The saphenous vein to be attached to the aorta is shown at 99.

Referring now to FIG. 8, there is shown generally at 100 a catheter with a uniquely designed balloon generally shown at 102. Catheter 100 is similar to catheter 10 shown in FIG. 2 and catheter 90 shown in FIG. 5, wherein like numerals refer to like elements. Balloon 102 is designed to allow even more control of the overall balloon diameter. The nominal state of the balloon 102 is shown in FIG. 8, wherein a resilient material 104, such as foam, determines the nominal diameter. When a pressure is applied to lumen 60, the overall diameter of the balloon can be increased approximately 20% beyond the nominal diameter, as shown in FIG. 10. The catheter 100 of the present invention is ideally suitable for occluding an aorta, however, the present invention finds suitable preferred use for occluding other body passageways, such as the trachea, and limitation to use in a vessel of the heart is not to be inferred by the present invention. The present invention is discussed with reference to occluding the aorta for illustration and clarity and for understanding the present invention.

Still referring to FIG. 8, catheter 100 is seen to have a catheter body 50 extending to a distal end 54, similar to catheter 10 in FIG. 2. Balloon 102 has a first resilient inner shell 106 disposed about the catheter body 50 and covering the opening 64 of lumen 60. The inner shell 106 is secured and sealed to catheter body 50 at each end thereof using a suitable adhesive, although heat could also be used to fuse the balloon shell 106 to the body of catheter 50. Disposed about the inner shell 106 is an oval or generally egg-shaped unitary piece of the resilient material 104, such as foam. An outer resilient shell 110 is seen to encapsulate the foam material 104, the foam material 104 residing between the inner shell 106 and the outer shell 110. The outer shell 110 is comprised of a resilient material similar to that of inner shell 106, and overlaps the sealed edges of inner shell 106. Outer shell 110 is slipped over and sealed to both the distal ends of inner shell 106 and also to the catheter body 50 using a suitable adhesive, although heat or other suitable attachment means is appropriate. A coating may be used in place of outer shell 110 if desired. The outer curvature of resilient material 104 defines the shape and diameter of the balloon 102.

Referring to FIG. 9, there is shown a cross section of the novel balloon 102 taken along line 9—9 in FIG. 8. The resilient foam material 104 is preferably comprised of an open-cell foam material, such as polyurethane, but could also comprise of a closed-cell material such as polyethylene if desired to eliminate the need for the outer shell 110. In this alternative embodiment, each end of the non-absorbing foam material 104 is sealed to the catheter body 50 to allow inner balloon 106 to expand under the closed-cell material. The inner shell 106 and outer shell 110 preferably comprise of a soft material such as silicone. The resilient material 104 is preferably harder and less resilient than the inner shell 106 and the outer shell 110 to facilitate expansion of the outer shell 110. The resilient material 104 may also comprise of a gel or other form changing material. The second perfusion lumen 70 is seen to extend the length of the catheter 100 and terminate at opening 72. The third lumen 80 can be provided as well if desired, terminating at proximate openings 82, as shown in FIG. 2.

Referring now to FIG. 10, there is shown catheter 100 with the balloon 102 in the expanded state when positive pressure is applied to the inner balloon shell 106 via the balloon lumen 60. The inner balloon shell 106 is seen to expand and define a cavity 116. As the inner shell 106 expands, this compresses the resilient foam material 104 outwardly, as shown, further stretching the outer shell 110 to increase the overall diameter of the balloon 102. Due to the resiliency of the resilient material 104, the resilient material 104 will compress slightly whereby a 20% expansion of the inner shell 106 causes about a 10% expansion of the outer shell 110, and thus a 10% increase of the diameter of the balloon 102. The overall expansion of the balloon 102 is a function of the pressure applied to the balloon lumen 60. The expansion of balloon 102 is generally linear with respect to the pressure applied to lumen 60. The further expansion of the balloon 102 beyond its nominal diameter is especially useful for fully occluding a body passageway, such as an aorta, when the nominal diameter of the balloon is not quite sufficient to occlude the vessel, but wherein further expansion of the balloon does suitably occlude the vessel to prevent fluid flow therethrough. Since the diameter of a body passageway, such as the aorta, can vary significantly from one patient to another, the present invention finds technical advantages by allowing the balloon 102 to customly fit to the inner diameter of a body passageway needing to be occluded, such as the aorta, a trachea, etc.

Referring now to FIG. 11, there is shown an alternative preferred balloon generally shown at 120. Balloon 120 is seen to be substantially identical to balloon 102 in FIG. 8, wherein like numerals refer to like elements. However, the resilient foam material 104 is seen to be radially partitioned into a plurality of segments 122 circumferentially about the catheter body 50. In the nonexpanded state, as shown in FIG. 10, the interfacing edges 124 of the sections 122 engage one another, as shown, with the overall diameter of the resilient material 104 being the same as that shown in FIG. 8. The interfacing edges 124 of sections 122 extend in the radial direction, as shown, with the width of each section 22 being approximately equal.

Referring to FIG. 12, there is shown the modified balloon 120 in the expanded state, whereby each of the resilient foam sections 122 are seen to be separated from one another by corresponding gaps 128. By partitioning the resilient foam section 104 into modular sections 122, this further facilitates the expansion of the foam material 104 in the radial direction when a pressure is applied via lumen 60. For a given pressure to lumen 60, the overall expansion of the foam material 104, and thus the outer shell 110, is increased from that of the embodiment in FIG. 8. For a given pressure, the balloon 102 of the embodiment of FIG. 8 may increase 10%, but the overall diameter of balloon 120 in the embodiment of FIG. 11 will increase about 20%. Each of the resilient material sections 122 are still encapsulated between the inner shell 106 and the outer shell 110, as described with regards to balloon 102 in FIG. 8.

Referring now to FIG. 13, yet another alternative embodiment of a catheter is shown generally at 130 having a balloon 131. Catheter 130 is generally the same as catheter 100 in FIG. 8, wherein like numerals refer to like elements. However, in contrast to the resilient foam sections 104 shown in FIG. 8 or FIG. 11, the resilient foam material 104 is partitioned into annular sections 132. Each of the annular sections 132 abut against each other along section edges 134, each section 132 being concentric with each other about the catheter body 50, as shown. A cross section of the modified balloon 131 taken along line 14—14 is shown in FIG. 14.

Referring to FIG. 14, there is shown the modified balloon 131 in its expanded state, whereby the inner shell 106 is expanded by applying a pressure via balloon 60. The inner shell 106 expands to define the inner cavity 116. As the inner shell 106 expands, each of the annular sections 132 expands outwardly, and separate from one another to define gaps 136. The expanding annular sections 132 expand radially outward to expand the outer shell 110, as shown, to further increase the overall diameter of the balloon 131. Similar to the partitioned foam material shown in FIG. 11, by partitioning the resilient material 104 to provide a modular resilient sections, the resilient material 104 will compress and expand more easily to increase the outer diameter of shell 110 for a given pressure to lumen 60. In addition, by providing modular annular sections 132, the curvature of the outer shell 110 will conform to the inner curvature of the body passageway that the balloon 131 is inserted into. For instance, if the inner wall of the aorta is curved, the outer diameter of the balloon 131 will conform to this curvature to fully occlude the passageway when inflated. Thus, the novel balloon 131 adapts to the particular patient into which it is inserted. Likewise, the modular sections 122 in FIG. 11 also allow the diameter of the balloon to also conform to the body passageway to fully occlude the passageway and prevent flow.

Figure 16:
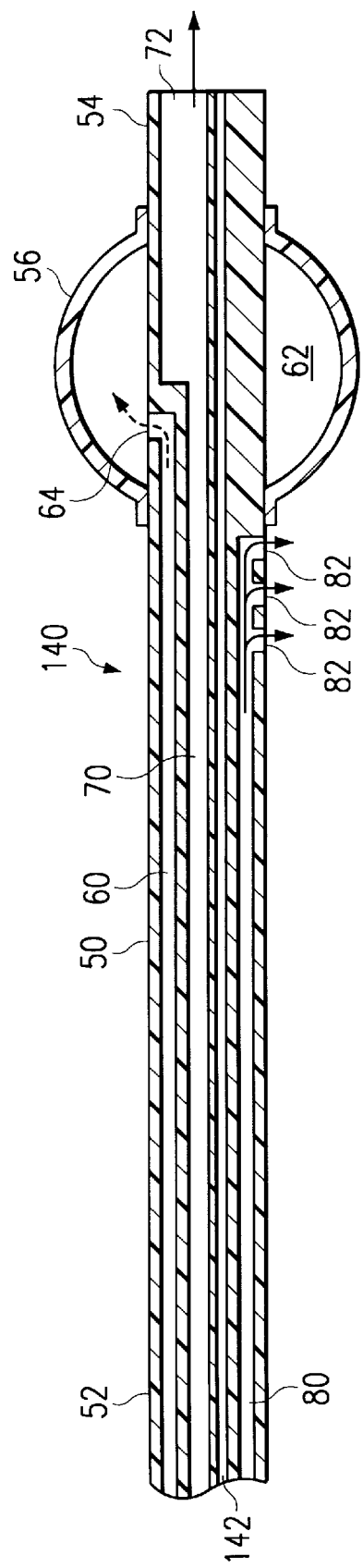
FIG. 16 is a sectional side view of a catheter having a fourth lumen for sensing pressure and/or venting the left ventricle of the heart when used in the orientation shown in FIG. 4.

Referring to FIG. 16, wherein like numerals refer to like elements, a catheter 140 having a fourth lumen 142, is provided through the catheter body 50 and terminate at the proximal end of the balloon, as shown, but could also be provided distal of the balloon, if desired, to provide for pressure sensing or venting during use. The fourth lumen allows a body passageway pressure to be ascertained which is desirable to determine if the balloon is occluding the passageway as intended. If the pressure detected via this fourth lumen 142 indicates that the balloon 56 is in its unexpanded state, or is not fully occluding the body passageway, pressure can be applied via lumen 60 to inflate the balloon, as shown in FIG. 10, FIG. 12 and FIG. 15 until the pressure reading indicates the passageway is fully occluded. The fourth lumen also allows venting of the left ventricle of excess cardioplegia and blood to protect the endocardium when the apex of the heart is elevated. The fourth lumen 142 also permits a malleable rod or material to be selectively inserted therein to facilitate customly shaping the curvature of the catheter body.

While the catheters having a unique balloon according to the embodiments shown in FIG. 8–FIG. 16 are ideally suited for use for occluding the aorta, and are also ideally suited for use with the catheters 10 and 90 for use as a multi-lumen catheter, the unique balloon catheters having a resilient material are well suited for performing other surgical procedures whereby clamping of a body passageway is desired. According to one embodiment of the present invention, a single lumen catheter having a unique balloon with a resilient interior can be provided for occluding a vessel, such as the trachea. Thus, the present invention is suitable for other percutaneous procedures besides aortic perfusion.

In summary, the alternative preferred embodiments shown in FIGS. 8–16 are suitable for implementation in the multi-lumen aortic clamp catheters of FIG. 2 and FIG. 5, but also have more general purpose uses to occlude any body passageway, including passageways having unique curvatures and/or varying diameters. The partitioned resilient sections in the embodiments of FIG. 11 and FIG. 15 are well suited to conform to the inner diameter of the passageway and fully occlude the passageway to prevent fluid flow therethrough. The additional expansion capabilities of the balloons including the resilient sections allows the catheter to conform to the particular passageway of many patients.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

We claim:

1. A method of providing cardiopulmonary bypass pump support during open heart surgery, wherein the heart has an ascending aorta, an aortic base, an aortic valve, an aortic arch, a coronary artery, and a subclavian artery, comprising the steps of:

a) inserting an infusion catheter having a proximal end and a distal end into the ascending aorta, the catheter having a first lumen, a second lumen and a third lumen each extending between said proximal end and said distal end, said catheter having an expandable balloon proximate said distal end, said first lumen in fluid communication with said balloon, said catheter having an infusion opening in fluid communication with said second lumen and located at said catheter distal end, said catheter having a cardioplegia opening in fluid communication with said third lumen defined adjacent said balloon between said balloon and said catheter proximal end wherein said balloon comprises a flexible inner shell disposed about said catheter, and a resilient material disposed about said inner shell adapted to conform to said ascending aorta, said first lumen being in fluid communication with said flexible inner shell;

b) advancing said infusion catheter upwardly into said ascending aorta such that said balloon is positioned above the aortic base and said catheter distal end including said infusion opening is positioned toward said aortic arch, said cardioplegia opening being positioned toward said aortic base;

c) infusing oxygenated blood into said aorta via said catheter second lumen through said infusion opening;

d) expanding said balloon to occlude said aorta with said resilient material compressing against and conforming to said aorta; and e) delivering a cardioplegia solution to said heart via said catheter third lumen through said cardioplegia opening to the heart.

2. The method as specified in claim 1 wherein said balloon is positioned in said step b) such that said balloon is positioned between the aortic base and the subclavian artery.

3. The method as specified in claim 1 wherein said oxygenated blood is delivered in said step c) using an extracorporeal circuit.

4. The method as specified in claim 1 wherein said catheter is held in place with respect to said aorta using purse string sutures.

5. The method as specified in claim 1 wherein said balloon is expanded in said step d) to occlude said aorta by inflating said balloon with a fluid until said balloon can be felt from outside the aorta.

6. The method as specified in claim 1 wherein said cardioplegia solution is delivered into the aorta between the aortic valve and said catheter balloon.

7. The method as specified in claim 1 wherein said catheter further comprises a fourth lumen extending from said proximal end to said distal end, further comprising the step of venting said heart via said fourth lumen.

8. The method as specified in claim 1 wherein said balloon further comprises a flexible outer shell disposed about said resilient material.

9. The method as specified in claim 8 wherein said resilient material comprises foam.

10. The method as specified in claim 1 wherein said resilient material is partitioned into sections, said sections interfacing one another along section edges.

11. The method as specified in claim 10 wherein said section edges extend longitudinally with respect to said catheter.

12. The method as specified in claim 10 wherein said section edges extend transverse with respect to said catheter.

13. The method as specified in claim 1 wherein said resilient material comprises a closed cell foam.

14. The method as specified in claim 1 further comprising the step of delivering oxygenated blood to said coronary artery via said cardioplegia opening.

15. The method as specified in claim 1 wherein said balloon has a pair of lobes defining a cavity therebetween in said aorta, further comprising the step of performing an anastomosis to said aorta proximate said cavity.

16. The method as specified in claim 15 wherein said pair of lobes are defined by an annular constriction about said balloon.

17. The method as specified in claim 1 wherein said catheter further comprises a fourth lumen extending from said proximal end to said distal end, further comprising the step of inserting a malleable material into said fourth lumen to permit shaping the curvature of said catheter.

18. A method of occluding a body passageway with a catheter having a catheter body extending between a proximal end and a distal end and having a lumen extending therethrough, said catheter having a balloon comprising a flexible inner shell disposed about said catheter, a resilient material disposed about said inner shell, and a continuous flexible outer shell sealingly disposed about said resilient material, comprising the steps of:

a) inserting said catheter into said body passageway; and b) inflating said balloon to occlude said body passageway.

19. The method as specified in claim 18 wherein said first lumen is in fluid communication with said flexible inner shell.

20. The method as specified in claim 18 wherein said resilient material comprises foam.

21. The method as specified in claim 19 wherein said resilient material is partitioned into sections, said sections interfacing one another along section edges.

22. The method as specified in claim 21 wherein said section edges extend longitudinally with respect to said catheter.

23. The method as specified in claim 21 wherein said section edges extend transverse with respect to said catheter.

24. The method as specified in claim 19 wherein said resilient material comprises a closed cell foam.

* * * * *